United States Patent [19]
Aoshima et al.

[11] 4,258,217
[45] Mar. 24, 1981

[54] PROCESS FOR PRODUCING METHACROLEIN

[75] Inventors: Atsushi Aoshima, Yokohama; Ryoichi Mitsui; Tatsuo Yamaguchi, both of Fuji, all of Japan

[73] Assignee: Asahi Kasei Kogyo Kabushiki Kaisha, Osaka, Japan

[21] Appl. No.: 83,878

[22] Filed: Oct. 11, 1979

[30] Foreign Application Priority Data

Oct. 13, 1978 [JP] Japan .................................. 53-125133
Nov. 6, 1978 [JP] Japan .................................. 53-135881

[51] Int. Cl.³ ........................ C07C 45/30; C07C 45/39
[52] U.S. Cl. ............................................................ 568/474
[58] Field of Search .................... 260/603 C; 568/474, 568/471

[56] References Cited

U.S. PATENT DOCUMENTS

| | | | |
|---|---|---|---|
| 3,716,497 | 2/1973 | Courty | 260/603 C |
| 4,035,418 | 7/1977 | Okada et al. | 260/603 C |
| 4,065,507 | 12/1977 | Hardman | 260/603 C |

FOREIGN PATENT DOCUMENTS 947772   5/1974   Canada ................................. 568/474

*Primary Examiner*—Werren B. Lone
*Attorney, Agent, or Firm*—Sprung, Felfe, Horn, Lynch & Kramer

[57] ABSTRACT

A process for producing methacrolein by oxidation of isobutylene or tert-butanol with molecular oxygen in the presence of a catalyst having the following composition:

$$Mo_{12}Bi_aFe_bNi_cPb_dX_fO_g \text{ or}$$

$$Mo_{12}Bi_aFe_bNi_cPb_dSm_eX_fO_g$$

wherein X represents at least one element selected from the group consisting of Rb, Cs and Tl; and when X represents at least two of the elements f is the sum of the elements; a is a value of 0.1 to 10; b is a value of 0.05 to 2; c is a value of 0.05 to 2; d is a value of 0.05 to 5; e is a value of 0.05 to 5; f is a value of 0.01 to 2; and g is the number of oxygen atoms satisfying the valencies of the elements. Said catalyst enables methacrolein to be produced in high yield and can prevent the formation of methacrylic acid.

8 Claims, 1 Drawing Figure

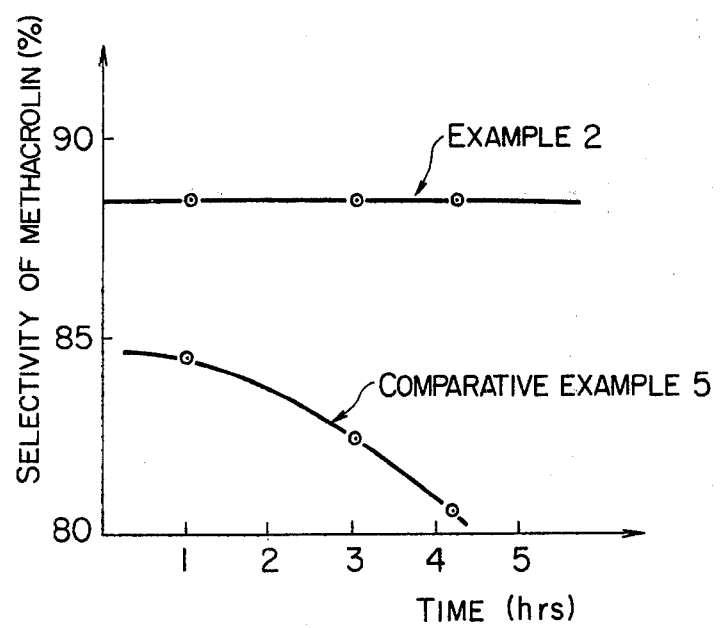

PROCESS FOR PRODUCING METHACROLEIN

This invention relates to a process for producing methacrolein in high yield by oxidizing isobutylene or tert-butanol with molecular oxygen with a specific catalyst.

Many catalysts have hitherto been proposed as catalysts for catalytic oxidation of isobutylene or tert-butanol in vapor phase. However, these catalysts still require improvement in many respects, from the industrial viewpoint. For example, the selectivity to methacrolein is low, and in addition, since when methacrolein is produced as a starting material for producing a polymer the methacrolein must be pure, isobutyraldehyde produced as by-product must be removed. However, since the boiling point of isobutyraldehyde (72.2° C.) is very near to that of methacrolein (73.5° C.), it is very difficult to separate methacrolein from the mixture thereof. Therefore, there has been desired a catalyst which produces isobutyraldehyde in an amount as small as possible. On the other hand, in respect of apparatus design, a lower ratio of oxygen to olefin is more desirable in view of safety and economy. However, with all the known catalysts, the reaction has to be effected at a relatively high oxygen ratio in order to avoid the decrease in the activity of catalysts. Thus, many problems have remained.

The present inventors have conducted extensive research for solving the above problems, and as a result, have found an excellent catalyst.

It is an object of this invention to provide a catalyst free from the above-mentioned defects.

It is another object of this invention to provide a process for producing methacrolein in a high yield with a specific catalyst.

Other objects and advantages of this invention will become apparent from the following description.

According to this invention, there is provided a process for producing methacrolein by oxidizing isobutylene or tert-butanol with molecular oxygen in the presence of a catalyst, characterized in that the catalyst has the following composition:

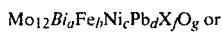

$Mo_{12}Bi_aFe_bNi_cPb_dX_fO_g$ or

$Mo_{12}Bi_aFe_bNi_cPb_dSm_eX_fO_g$ wherein X represents at least one element selected from the group consisting of Rb, Cs, and Tl; and when X represents at least two of the elements f is the sum of the elements; and a is a value of 0.1 to 10; b is a value of 0.05 to 2; c is a value of 0.05 to 2; d is a value of 0.05 to 5; e is a value of 0.05 to 5; f is a value of 0.01 to 2; and g represents the number of oxygen atoms satisfying the valences of the elements.

A characteristic feature of this invention is that the amount of methacrylic acid produced is relatively small and the selectivity to methacrolein is very high. Accordingly, the methacreolein produced by the process of this invention is most suitable as a starting material for producing methyl methacrylate directly from methacrolein. Another feature is that the formation of isobutyraldehyde which is difficult to separate from methacrolein can be prevented greatly. Also, the amount of acetic acid produced as by-product is small, and therefore, the treatment of the waste water is easy. Furthermore, with the catalyst of this invention, the reaction can be effected at a relatively low oxygen to olefin ratio as compared with the conventional catalysts, and therefore, it can be understood that the catalyst of this invention is very excellent as an industrial catalyst even in the respects of safety and economy.

One of the characteristic components of the present catalyst composition that can bring about the above-mentioned effects is lead. The first effect of addition of lead is to improve remarkably the catalyst performance (particularly, the selectivity to methacrolein). The incorporation of lead into the catalysst enables the prevention of the complete oxides ($CO+CO_2$) from being formed and remarkable enhancement of the selectivity to methacrolein. Lead contributes particularly remarkably to the above-mentioned effects. The substitution of, for example, tin, germanium, indium, manganese, lanthanum or the like for the lead brings about only the same result as when no lead is incorporated or rather decrease in selectivity to methacrolein. The second effect of addition of lead is that even when the reaction is effected at a relatively small ratio of oxygen to isobutylene or tert-butanol the catalyst performance is maintained for a long period of time. This seems to be because lead has a very high affinity to oxygen and can well catch oxygen into the catalyst even at a low oxygen concentration. Accordingly, the lead-containing catalyst system is more resistant against a reducing atmosphere than a lead-free catalyst system, and enables the reaction to be effected at a low oxygen to isobutylene or tert-butanol ratio. Moreover, when samarium is used together with lead, the production of by-products such as acetaldehyde, propionaldehyde, acetone, acetic acid and the like can be prevented.

The other characteristic component of the present catalyst composition is nickel. The incorporation of a small amount of nickel into the catalyst composition results in a great improvement in activity, and it is observed that the activity is increased with an increase of the amount of nickel. However, the addition of a large amount of nickel is disadvantageous in that the selectivity to methacrolein is decreased and not only is the amount of such by-products as methacrylic acid, acetic acid and the like increased, but the amount of isobutyraldehyde formed as by-product is also increased.

It is very difficult to separate isobutyraldehyde from methacrolein because the difference in boiling point between the two is only 2° C., and when methacrolein containing a large amount of isobutyraldehyde is used as the starting material for producing methyl methacrylate, methyl isobutyrate is simultaneously formed, and hence the resulting ester does not meet the standard for the starting material of polymerization. It is very important for an industrial catalyst that the formation of the by-product isobutyraldehyde is maintained as low as possible.

It has been found that when in the catalyst composition of this invention the proportion of nickel is more than 2, isobutyraldehyde is formed in an amount as large as 200 to 3,000 parts per million parts of methacrolein, and it is converted to methyl isobutyrate in the production of methyl methacrylate, resulting in deterioration of the quality of methyl methacrylate. When the amount of isobutyraldehyde formed is kept less than 200 ppm., substantially satisfactory methyl methacry polymer can be obtained. In order to obtain a higher quality polymer, it is preferred to keep the nickel content in the catalyst in the range of 0.25 to 1.5.

The proportion of iron in the catalyst composition is 0.05 to 2, and in order to make it possible to produce methacrolein stably in high yield for a longer period of time, the proportion of iron to nickel is preferably maintained at 0.25 to 2.

The X component is selected from the group consisting of thallium, rubidium, and cesium, among which rubidium and cesium are preferred. The X component is essential in the present catalyst. With a system free from the X component or a system containing other alkali, for example, Na or Li, the selectivity to methacrolein is extremely low.

As a carrier for the present catalyst, there may be used known carriers such as silica sol, silica gel, silicon carbide, alumina and the like, and in particular, silica sol and silica gel are excellent.

The catalyst of this invention can be prepared by, for example, the following method: Water-soluble compounds of bismuth, iron, nickel, and rubidum (and/or a water-soluble compound of cesium) and a water-soluble lead compound are added to an aqueous ammonium molybdate solution, and silica sol is further added as the carrier, after which the mixture is evaporated to dryness on a water bath and then subjected to preliminary calcination and main calcination in the presence of a molecular oxygen-containing gas such as oxygen and air. In general, the temperature of the preliminary calcination is 100° to 500° C., preferably 200° to 400° C. The temperature for the main calcination is typically 400° to 1,000° C., preferably 500° to 700° C., more preferably 500° to 630° C.

The starting materials of the respective elements used in the preparation of the catalyst of this invention may be not only oxides but also in any form which can be converted into the constituents of the present catalyst by calcination. Inorganic acid salts, for example, ammonium salts, nitrates, carbonates and the like; acetates; condensed acids of the elements may be used as the compounds of the elements.

The catalysts may be used in the form of granules, tablets or powder. The reactor may be of the fixed bed type or the fluidized bed type. The reaction may be effected at a temperature of 250° to 550° C., preferably 350° to 450° C. under a pressure of 0.5 to 10 atms., preferably from atmospheric pressure to 2 atms. The time for which the starting mixed gas of isobutylene or tert-butanol; a molecular oxygen-containing gas; steam; and an inert gas contacts with the catalyst (referred to hereinafter as contact time) is 0.1 to 15 sec, preferably 0.2 to 10 sec, under atmospheric pressure. The flow rate of the starting mixed gas to the catalyst is a space velocity of 100 to 5,000 hr$^{-1}$, preferably 200 to 2,000 hr$^{-1}$. The composition of the mixed gas is 0.5 to 4 moles, preferably 1.4 to 2.5 moles, of oxygen and 1 to 30 moles, preferably 2 to 15 moles, of steam, per mole of isobutylene or tert-butanol. The amount of the inert gas, for example, $N_2$, He, Ar, $CO_2$, after-reaction recycle gas or the like, may be varied depending upon the amounts of the other gases. The catalyst of this invention exhibits substantially the same result of reaction regardless of whether the starting material is isobutylene or tert-butanol.

The catalyst of this invention is more excellent in selectivity to methacrolein than the hitherto proposed catalysts, and produces only a very small amount of isobutyraldehyde which is very difficult to separate from methacrolein. Moreover, the catalyst of this invention does not contain those metals which have strong toxicity, such as arsenic, tellurium and the like, and enables the reaction to be conducted at a low oxygen ratio. Therefore, it can be understood that the present catalyst composition is very excellent as an industrial catalyst.

This invention is further illustrated below referring to Examples and the accompanying drawing, which shows relationship between selectivity to methacrolein and the elapsed time in Example 2 and Comparative Example 5 which appear hereinafter. However, it should not be understood that this invention is restricted to the Examples.

EXAMPLE 1

In 200 ml of distilled water was dissolved 21.2 g of ammonium paramolybudate, and 0.31 g of rubidium nitrate was then dissolved therein. The resulting solution is referred to hereinafter as Solution A.

In 200 ml of distilled water was dissolved 2.9 g of nickel nitrate, after which 4.04 g of ferric nitrate and 3.31 g of lead nitrate were then dissolved therein. The resulting solution was mixed with Solution A, and to the resulting mixture was added 32.77 g of silica sol (Cataloid 20H, a trade name of Shokubai Kasei Kabushiki Kaisha). To the resulting mixture was added with stirring an aqueous nitric acid solution containing 4.84 g of bismuth nitrate. The resulting solution was subsequently evaporated to dryness on a water bath, and then subjected to preliminary calcination in air at 300° C. for 2 hrs. The calcination product thus obtained was pulverized to 10 to 28 mesh (Tyler), and thereafter calcined in air at 620° C. for 4 hrs. The composition of the catalyst thus obtained was $Mo_{12}Bi_1Fe_1Ni_1Pb_1Rb_{0.2}O_x$.

A pyrex reactor having an inner diameter of 5 mm was filled with 5 g of the thus obtained catalyst, and a mixed gas consisting of isobutylene, $O_2$, $H_2O$ and He in a molar ratio of 3:6:20:71 was passed through the reactor at a contact time of 2.5 sec at a temperature of 360° to 450° C. to effect the reaction. When the reaction temperature was 400° C., the conversion of isobutylene was 94.2% and the methacrolein selectivity was 90.0%. The result obtained is shown in Table 1.

COMPARATIVE EXAMPLE 1

A catalyst was prepared in the same manner as in Example 1, except that the lead nitrate was not added, and the same reaction as in Example 1 was effected with the catalyst. The result thus obtained is shown in Table 1.

COMPARATIVE EXAMPLE 2

A catalyst was prepared in the same manner as in Example 1, except that 3.34 g of tin chloride was substituted for the lead nitrate, and the same reaction as in Example 1 was effected with the thus obtained catalyst. The result obtained is shown in Table 1.

COMPARATIVE EXAMPLE 3

A catalyst was prepared in the same manner as in Example 1, except that 1.05 g of germanium oxide was substituted for the lead nitrate, and the same reaction as in Example 1 was effected with the catalyst thus obtained. The result obtained is shown in Table 1.

TABLE 1

|  | Composition | Reaction temp. (°C.) | Conversion (%) | Selectivity to MAcr (%) | Selectivity to CO + CO$_2$ (%) | MAA selectivity (%) |
|---|---|---|---|---|---|---|
| Example 1 | Mo$_{12}$Bi$_1$Fe$_1$Ni$_1$Pb$_1$Rb$_{0.2}$ | 400 | 94.2 | 90.0 | 5.0 | 2.3 |
| Comp. Ex. 1 | Mo$_{12}$Bi$_1$Fe$_1$Ni$_1$Rb$_{0.2}$ | 380 | 94.4 | 85.5 | 8.2 | 2.2 |
| Comp. Ex. 2 | Mo$_{12}$Bi$_1$Fe$_1$Ni$_1$Sn$_1$Rb$_{0.2}$ | 400 | 88.6 | 83.1 | 9.3 | 4.5 |
| Comp. Ex. 3 | Mo$_{12}$Bi$_1$Fe$_1$Ni$_1$Ge$_1$Rb$_{0.2}$ | 400 | 60.7 | 85.2 | 9.4 | 1.8 |

Note:
MAcr means methacrolein.
MAA means methacrylic acid.

EXAMPLE 2

The catalyst prepared in Example 1 was put in a pyrex reaction tube having an inner diameter of 5 mm, and a mixed gas consisting of isobutylene, O$_2$, H$_2$O and N$_2$ in a molar ratio of 5:7:20:68 was passed through the tube at 420° C. at a contact time of 2.5 sec to subject the mixture to reaction. The result was as shown in the accompanying drawing.

COMPARATIVE EXAMPLE 5

Reaction was effected under the same conditions as in Example 2, except that the reaction temperature was 400° C. instead of 420° C., to obtain the result shown in the accompanying drawing.

EXAMPLE 3

A catalyst was prepared in the same manner as in Example 1, except that 0.31 g of rubidium nitrate and 2.22 g of samarium were substituted for the bismuth nitrate, and the same reaction as in Example 1 was effected, except that the reaction temperature was as shown in Table 2, to obtain the result shown in Table 2.

EXAMPLES 5 TO 11

Catalysts were prepared under the same conditions as in Example 1, except that the proportions of elements were changed as shown in Table 2, and the same reaction as in Example 1 was conducted with the catalysts obtained, except that the reaction temperature was varied as shown in Table 2, to obtain the results shown in Table 2.

COMPARATIVE EXAMPLES 6 TO 11

Catalysts were prepared under the same conditions as in Example 1, except that the kind and proportion of elements were varied as shown in Table 2, and the same reaction as in Example 1 was effected with the resulting catalysts, except that the reaction temperature was varied, to obtain the result shown in Table 2.

EXAMPLES 12 TO 21

Catalysts were prepared in the same manner as in Example 1, except that the kind and proportion of the elements were varied as in Table 3, and reaction was effected with the resulting catalysts under the same conditions as in Example 1, except that tert-butanol was substituted for the isobutylene, to obtain the results shown in Table 3.

COMPARATIVE EXAMPLES 12 TO 18

Catalysts were prepared in the same manner as in Example 1, except that the kind and proportion of the elements were varied as shown in Table 3, and the same reaction as in Examples 12 to 21 was conducted with the resulting catalysts, to obtain the results shown in Table 3.

EXAMPLES 22 TO 23

The same reaction as in Example 1 was effected with the same catalyst as in Example 1 (Example 22) or with a catalyst prepared in the same manner as in Example 1, except that the proportion of Ni was varied as shown in Table 4 (Example 23), to check the formation of isobutyraldehyde and acetic acid, thereby obtaining the results shown in Table 4.

COMPARATIVE EXAMPLES 19 TO 22

Under the same conditions as in Examples 22 to 23, the formation of isobutyraldehyde and acetic acid was checked with the catalysts shown in Table 4, to obtain the results shown in Table 4.

TABLE 2

| | | Oxidation of isobutylene | | | | |
|---|---|---|---|---|---|---|
| Example No. | Composition | Reaction temp. (°C.) | Conversion (%) | MAcr selectivity (%) | CO + CO$_2$ selectivity (%) | MAA selectivity (%) |
| 3 | Mo$_{12}$Bi$_1$Fe$_1$Ni$_1$Rb$_{0.2}$Sm$_1$Pb$_1$ | 440 | 93.6 | 90.3 | 6.1 | 2.1 |
| 4 | Mo$_{12}$Bi$_{0.5}$Fe$_1$Ni$_1$Rb$_{0.2}$Pb$_1$ | 420 | 90.1 | 89.4 | 6.3 | 2.1 |
| 5 | Mo$_{12}$Bi$_1$Fe$_1$Ni$_1$Tl$_{0.2}$Pb$_1$ | 400 | 86.9 | 88.5 | 7.0 | 1.7 |
| 6 | Mo$_{12}$Bi$_1$Fe$_1$Ni$_1$Rb$_{0.4}$Pb$_1$ | 400 | 91.8 | 90.0 | 5.5 | 2.4 |
| 7 | Mo$_{12}$Bi$_1$Fe$_1$Ni$_1$Cs$_{0.2}$Pb$_1$Sm$_{0.5}$ | 420 | 92.0 | 88.9 | 7.6 | 2.6 |
| 8 | Mo$_{12}$Bi$_1$Fe$_1$Ni$_1$Cs$_{0.2}$Pb$_1$ | 380 | 90.8 | 87.4 | 7.0 | 2.7 |
| 9 | Mo$_{12}$Bi$_1$Fe$_1$Ni$_1$Rb$_{0.2}$Pb$_4$ | 420 | 91.5 | 88.5 | 7.3 | 2.3 |
| 10 | Mo$_{12}$Bi$_1$Fe$_2$Ni$_1$Rb$_{0.2}$Pb$_1$ | 420 | 85.0 | 89.0 | 7.2 | 2.3 |
| 11 | Mo$_{12}$Bi$_1$Fe$_1$Ni$_1$Rb$_{1.0}$Pb$_1$ | 400 | 93.1 | 89.2 | 5.6 | 2.4 |
| Comp. Ex. 6 | Mo$_{12}$Bi$_1$Fe$_1$Ni$_1$Na$_{0.2}$Pb$_1$ | 380 | 90.5 | 64.3 | 22.6 | 4.6 |
| Comp. Ex. 7 | Mo$_{12}$Bi$_1$Fe$_1$Ni$_1$Tl$_{0.2}$ | 380 | 92.5 | 76.0 | 10.5 | 2.0 |
| Comp. Ex. 8 | Mo$_{12}$Bi$_1$Fe$_{11}$Ni$_1$Pb$_1$Rb$_{0.2}$P$_1$ | 460 | 68.5 | 76.3 | 29.8 | 1.8 |
| Comp. Ex. 9 | Mo$_{12}$Bi$_1$Fe$_1$Ni$_1$Pb$_1$ | 400 | 90.0 | 59.4 | 29.5 | 5.8 |
| Comp. Ex. 10 | Mo$_{12}$Bi$_{2.7}$Fe$_1$Ni$_1$Pb$_{9.5}$Rb$_{0.2}$ | 420 | 52.2 | 75.0 | 19.0 | 2.1 |

TABLE 2-continued

| | | Oxidation of isobutylene | | | | |
|---|---|---|---|---|---|---|
| Example No. | Composition | Reaction temp. (°C.) | Conversion (%) | MAcr selectivity (%) | CO + CO$_2$ selectivity (%) | MAA selectivity (%) |
| Comp. Ex. 11 | Mo$_{12}$Bi$_{11}$Fe$_1$Ni$_1$Pb$_1$Rb$_{0.2}$ | 440 | 42.3 | 65.8 | 28.7 | 2.5 |

Note:
MAcr means methacrolein.
MAA means methacrylic acid.

TABLE 3

| | | Oxidation of tert-butanol | | | | |
|---|---|---|---|---|---|---|
| Example No. | Composition | Reaction temp. (°C.) | Conversion (%) | MAcr selectivity (%) | CO + CO$_2$ selectivity (%) | MAA selectivity (%) |
| 12 | Mo$_{12}$Bi$_1$Fe$_1$Ni$_1$Pb$_1$Rb$_{0.2}$ | 400 | 94.0 | 89.8 | 5.1 | 2.4 |
| 13 | Mo$_{12}$Bi$_1$Fe$_1$Ni$_1$Pb$_1$Rb$_{0.2}$Sm$_{0.5}$ | 440 | 93.5 | 90.4 | 6.1 | 2.3 |
| 14 | Mo$_{12}$Bi$_1$Fe$_1$Ni$_1$Rb$_{1.0}$Pb$_1$ | 400 | 93.1 | 89.3 | 5.4 | 2.3 |
| 15 | Mo$_{12}$Bi$_1$Fe$_1$Ni$_1$Tl$_{0.2}$Pb$_1$ | 400 | 86.4 | 88.7 | 6.8 | 1.8 |
| 16 | Mo$_{12}$Bi$_1$Fe$_1$Ni$_1$Cs$_{0.2}$Pb$_1$ | 380 | 90.6 | 87.5 | 7.0 | 2.5 |
| 17 | Mo$_{12}$Bi$_1$Fe$_1$Ni$_1$Cs$_{0.2}$Pb$_1$Sm$_{0.5}$ | 420 | 91.9 | 88.8 | 7.7 | 2.6 |
| 18 | Mo$_{12}$Bi$_{0.5}$Fe$_1$Ni$_1$Rb$_{0.2}$Pb$_1$ | 420 | 89.5 | 89.5 | 6.2 | 2.0 |
| 19 | Mo$_{12}$Bi$_1$Fe$_1$Ni$_1$Rb$_{0.2}$Pb$_4$ | 420 | 91.8 | 88.3 | 7.5 | 2.3 |
| 20 | Mo$_{12}$Bi$_1$Fe$_2$Ni$_1$Rb$_{0.2}$Pb$_1$ | 420 | 84.8 | 89.1 | 7.1 | 2.3 |
| 21 | Mo$_{12}$Bi$_1$Fe$_1$Ni$_2$Rb$_{0.2}$Pb$_1$ | 400 | 94.6 | 86.8 | 7.1 | 3.1 |
| Comp. Ex. 12 | Mo$_{12}$Bi$_1$Fe$_1$Ni$_1$Rb$_{0.2}$ | 380 | 94.4 | 85.4 | 8.2 | 2.3 |
| Comp. Ex. 13 | Mo$_{12}$Bi$_1$Fe$_1$Ni$_1$Tl$_{0.2}$ | 380 | 91.6 | 77.1 | 9.9 | 2.1 |
| Comp. Ex. 14 | Mo$_{12}$Bi$_1$Fe$_1$Ni$_1$Pb$_1$ | 400 | 89.8 | 59.4 | 29.3 | 6.1 |
| Comp. Ex. 15 | Mo$_{12}$Bi$_1$Fe$_1$Ni$_1$Na$_{0.2}$Pb$_1$ | 380 | 90.1 | 64.7 | 22.4 | 4.6 |
| Comp. Ex. 16 | Mo$_{12}$Bi$_1$Fe$_1$Ni$_1$Rb$_{0.2}$Sn$_1$ | 400 | 88.6 | 83.0 | 9.2 | 4.6 |
| Comp. Ex. 17 | Mo$_{12}$Bi$_1$Fe$_1$Ni$_1$Rb$_{0.2}$Ge$_1$ | 400 | 60.8 | 85.1 | 9.3 | 1.9 |
| Comp. Ex. 18 | Mo$_{12}$Bi$_1$Fe$_{11}$Ni$_1$Pb$_1$Rb$_{0.2}$P$_1$ | 460 | 68.5 | 76.2 | 29.8 | 1.9 |

TABLE 4

| Example No. | Composition | Conversion (%) | MAcr selectivity (%) | Isobutyraldehyde selectivity (%) | Acetic acid selectivity (%) |
|---|---|---|---|---|---|
| 22 | Mo$_{12}$Bi$_1$Fe$_1$Ni$_1$Pb$_1$Rb$_{0.2}$ | 94.2 | 90.0 | 100 ppm. or less | 0.9 |
| 23 | Mo$_{12}$Bi$_1$Fe$_1$Ni$_2$Pb$_1$Rb$_{0.2}$ | 93.0 | 87.0 | ca. 200 ppm. | 1.4 |
| Comp. Ex. 19 | Mo$_{12}$Bi$_1$Fe$_1$Ni$_8$Pb$_1$Rb$_{0.2}$ | 96.0 | 79.0 | ca. 800 ppm. | 2.7 |
| Comp. Ex. 20 | Mo$_{12}$Bi$_1$Fe$_1$Ni$_1$Rb$_{0.2}$ | 94.4 | 85.5 | 100 ppm. or less | 1.2 |
| Comp. Ex. 21 | Mo$_{12}$Bi$_1$Fe$_1$Ni$_4$Rb$_{0.2}$ | 91.9 | 84.5 | ca. 350 ppm. | 2.0 |
| Comp. Ex. 22 | Mo$_{12}$Bi$_1$Fe$_1$Ni$_8$Rb$_{0.2}$ | 95.8 | 78.5 | ca. 800 ppm. | 2.8 |

What is claimed is:

1. A process for producing methacrolein by oxidizing isobutylene or tert-butanol with molecular oxygen with a catalyst at a temperature up to 550° C. and a pressure up to 10 atmospheres, characterized in that the catalyst has the following composition:

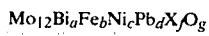

$$Mo_{12}Bi_aFe_bNi_cPb_dX_fO_g$$

wherein X is at least one element selected from the group consisting of Rb, Cs, and Tl; and when X represents at least two of the elements f represents the sum of the elements; a is a value of 0.1 to 10; b is a value of 0.05 to 2; c is a value of 0.05 to 2; d is a value of 0.05 to 5; f is a value of 0.01 to 2; and g represents the number of oxygen atoms satisfying the valences of the elements.

2. A process for producing methacrolein by oxidizing isobutylene or tert-butanol with molecular oxygen with a catalyst at a temperature up to 550° C. and a pressure up to 10 atmospheres, characterized in that the catalyst has the following composition:

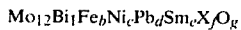

$$Mo_{12}Bi_aFe_bNi_cPb_dSm_eX_fO_g$$

wherein X represents at least one element selected from the group consisting of Rb, Cs and Tl; when X represents at least two of the elements f represents the sum of the elements; and a is a value of 0.1 to 10; b is a value of 0.05 to 2; c is a value of 0.05 to 2; d is a value of 0.05 to 5; e is a value of 0.05 to 5; f is a value of 0.01 to 2; and g represents the number of oxygen atoms satisfying the valences of the elements.

3. A process according to claim 1 or 2, wherein the catalyst is supported on silica.

4. A process according to claim 1, wherein the catalyst is in the form of a fixed bed or a fluidized bed.

5. A process according to claim 1 or 2, wherein the reaction is effected at a temperature of 250° to 550° C. at a pressure of 0.5 to 10 atms.

6. A process according to claim 1 or 2, wherein the reaction is effected at a temperature of 350° to 450° C. at a pressure of 1 to 2 atms.

7. A process according to claim 1 or 2, wherein a mixed gas consisting of isobutylene or tert-butanol, a molecular oxygen-containing gas, steam and an inert gas is connected with the catalyst for a period of 0.1 to 15 sec.

8. A process according to claim 7, wherein the mixed gas contains isobutylene or tert-butanol, oxygen and steam in a molar ratio of 1:0.5-4:1-30.

* * * * *